(12) United States Patent
Hansell et al.

(10) Patent No.: US 8,685,103 B2
(45) Date of Patent: Apr. 1, 2014

(54) TRANSFORAMINAL PROSTHETIC SPINAL DISC APPARATUS

(75) Inventors: Noah Hansell, King of Prussia, PA (US); Jeff Bennett, Pottstown, PA (US); David C. Paul, Phoenixville, PA (US)

(73) Assignee: Globus Medical, Inc., Audubon, PA (US)

( * ) Notice: Subject to any disclaimer, the term of this patent is extended or adjusted under 35 U.S.C. 154(b) by 2 days.

(21) Appl. No.: 13/557,292

(22) Filed: Jul. 25, 2012

(65) Prior Publication Data

US 2012/0290093 A1    Nov. 15, 2012

Related U.S. Application Data

(63) Continuation of application No. 12/632,267, filed on Dec. 7, 2009, now Pat. No. 8,277,509.

(51) Int. Cl.
*A61F 2/44*        (2006.01)

(52) U.S. Cl.
USPC ...................................... 623/17.16

(58) Field of Classification Search
CPC ........................................ A61F 2/44
USPC ................. 623/17.11–17.16; 606/246–249
See application file for complete search history.

(56) References Cited

U.S. PATENT DOCUMENTS

| | | |
|---|---|---|
| 4,759,766 A | 7/1988 | Buettner-Janz et al. |
| 4,997,432 A | 3/1991 | Keller |
| 5,122,130 A | 6/1992 | Keller |
| 5,246,458 A | 9/1993 | Graham |
| 5,258,031 A | 11/1993 | Salib et al. |
| 5,314,477 A | 5/1994 | Marnay |
| 5,401,269 A | 3/1995 | Buttner-Janz et al. |
| 5,425,773 A | 6/1995 | Boyd et al. |
| 5,507,816 A | 4/1996 | Bullivant |
| 5,534,029 A | 7/1996 | Shima |
| 5,556,431 A | 9/1996 | Buttner-Janz |
| 5,562,738 A | 10/1996 | Boyd et al. |
| 5,676,701 A | 10/1997 | Yuan et al. |
| 5,683,465 A | 11/1997 | Shinn et al. |
| 5,755,796 A | 5/1998 | Ibo |
| 5,888,226 A | 3/1999 | Rogozinski |
| 5,895,428 A | 4/1999 | Berry |
| 5,899,941 A | 5/1999 | Nishijima et al. |

(Continued)

FOREIGN PATENT DOCUMENTS

| | | |
|---|---|---|
| WO | 9905995 | 2/1999 |
| WO | 0023015 | 4/2000 |
| WO | 0042944 | 7/2002 |

*Primary Examiner* — Pedro Philogene
*Assistant Examiner* — David Comstock

(57) ABSTRACT

An intervertebral prosthetic implant having a first endplate having a first surface configured to substantially engage with a first vertebral body and a second surface having an extension with a concave contact surface, the concave contact surface being spaced apart from the second surface. A second endplate is provided with a first surface configured to substantially engage with a second vertebral body and a second surface comprising a convex contact surface, and the second endplate having a securing element positioned along and above the second surface defining a first and second window on opposing sides of the second surface. The securing element extends along the width and length of the lower endplate and configured with an access hole. An extension portion extends from the first surface of the first endplate through the access hole of the securing element and contacts the second surface of the second endplate.

20 Claims, 13 Drawing Sheets

(56) References Cited

U.S. PATENT DOCUMENTS

| | | |
|---|---|---|
| 6,063,121 A | 5/2000 | Xavier et al. |
| 6,080,157 A | 6/2000 | Cathro |
| 6,113,637 A | 9/2000 | Gill |
| 6,146,421 A | 11/2000 | Gordon |
| 6,146,422 A | 11/2000 | Lawson |
| 6,156,067 A | 12/2000 | Bryan |
| 6,228,118 B1 | 5/2001 | Gordon |
| 6,368,350 B1 | 4/2002 | Erickson |
| 6,375,682 B1 | 4/2002 | Fleischmann |
| 6,416,551 B1 | 7/2002 | Keller |
| 6,468,310 B1 | 10/2002 | Ralph |
| 6,540,785 B1 | 4/2003 | Gill |
| 6,635,087 B2 | 10/2003 | Angelucci |
| 6,660,007 B2 | 12/2003 | Khanna |
| 6,682,562 B2 | 1/2004 | Viart |
| 6,706,068 B2 | 3/2004 | Ferree |
| 6,712,852 B1 | 3/2004 | Chung |
| 6,997,953 B2 | 2/2006 | Chung |
| 2002/0035400 A1 | 3/2002 | Bryan |
| 2002/0111681 A1 | 8/2002 | Ralph |
| 2002/0111682 A1 | 8/2002 | Ralph |
| 2002/0111683 A1 | 8/2002 | Ralph |
| 2002/0111684 A1 | 8/2002 | Ralph |
| 2002/0111685 A1 | 8/2002 | Ralph |
| 2002/0111686 A1 | 8/2002 | Ralph |
| 2002/0111687 A1 | 8/2002 | Ralph |
| 2002/0120335 A1 | 8/2002 | Angelucci |
| 2003/0045935 A1 | 3/2003 | Angelucci |
| 2003/0045936 A1 | 3/2003 | Angelucci |
| 2003/0125738 A1 | 7/2003 | Khanna |
| 2003/0125740 A1 | 7/2003 | Khanna |
| 2003/0204261 A1 | 10/2003 | Eisermann |
| 2003/0233094 A1 | 12/2003 | Squires |
| 2004/0030388 A1 | 2/2004 | Null |
| 2004/0064184 A1 | 4/2004 | Chung |
| 2004/0117022 A1 | 6/2004 | Marnay |
| 2004/0138750 A1 | 7/2004 | Mitchell |
| 2004/0143332 A1 | 7/2004 | Krueger |
| 2004/0153155 A1 | 8/2004 | Chung |
| 2004/0153157 A1 | 8/2004 | Keller |
| 2004/0172133 A1 | 9/2004 | Gerber |
| 2004/0172135 A1 | 9/2004 | Mitchell |
| 2004/0210222 A1 | 10/2004 | Angelucci |
| 2004/0215198 A1 | 10/2004 | Marnay et al. |
| 2004/0220582 A1 | 11/2004 | Keller |
| 2004/0225365 A1 | 11/2004 | Eisermann |
| 2004/0243240 A1 | 12/2004 | Beaurain |
| 2005/0021145 A1 | 1/2005 | De Villiers |
| 2005/0038511 A1 | 2/2005 | Martz |
| 2005/0043800 A1 | 2/2005 | Paul |
| 2005/0107877 A1 | 5/2005 | Blain |
| 2005/0131412 A1 | 6/2005 | Olevsky |
| 2005/0251138 A1 | 11/2005 | Boris |
| 2005/0261773 A1 | 11/2005 | Ferree |
| 2005/0273100 A1 | 12/2005 | Taylor |
| 2006/0036325 A1 | 2/2006 | Paul |
| 2006/0064107 A1* | 3/2006 | Bertagnoli et al. ............ 606/99 |
| 2006/0116768 A1 | 6/2006 | Krueger |
| 2007/0010826 A1 | 1/2007 | Rhoda |

* cited by examiner

TRANSFORAMINAL PROSTHETIC SPINAL DISC APPARATUS

CROSS REFERENCE TO RELATED APPLICATIONS

This patent application is a continuation application claiming priority to U.S. patent application Ser. No. 12/632,267, filed Dec. 7, 2009 now U.S. Pat. No. 8,277,509, the entire contents of which are incorporated by reference.

FIELD OF THE INVENTION

The present invention relates to a prosthetic spinal disc for fully or partially replacing a damaged disc between two vertebrae of a spine. The present invention also relates to a method for implanting a prosthetic spinal disc via transforaminal implantation.

BACKGROUND OF THE INVENTION

As an alternative to vertebral fusion, various prosthetic discs have been developed. The first prosthetics embodied a wide variety of ideas, such as ball bearings, springs, metal spikes and other perceived aids. These prosthetics are all made to replace the entire intervertebral disc space.

One approach to the intervertebral space is the transforaminal approach. This approach has been used in interbody lumbar fusion surgeries and involves approaching the intervertebral space through the intervertebral foramina. This approach often requires the removal of one facet joint on either the left or right side. After removal, the surgeon gains access to the intervertebral space through the intervertebral foramina. One drawback to this method is that the removal of a facet joint may lead to instability of the spine. Despite this drawback, in many instances the transforaminal approach is favored in that there is reduced risk to the organs and greater vessels (as compared to the anterior approach) and reduced risk to the spinal cord (as to the posterior approach).

Once a spinal disc is positioned, there may be a need to limit the motion of the disc and convert the disc implant into a fusion implant. This generally requires the removal of the disc and the insertion of additional implants. Therefore there is a need for a single implant that can be utilized to convert prosthetic disc into a fusion device tailored for use in a transforaminal approach.

SUMMARY OF THE INVENTION

The present invention generally relates to an intervertebral prosthetic implant having a first endplate having a first surface configured to substantially engage with a first vertebral body and a second surface having an extension with a concave contact surface, the concave contact surface being spaced apart from the second surface. A second endplate is provided with a first surface configured to substantially engage with a second vertebral body and a second surface comprising a convex contact surface, and the second endplate having first and second side rails positioned along and above the second surface defining a first and second arcuate slots on opposing sides of the second surface. A plate connects the first and second endplates to restrict motion between the first and second endplates. The concave contact surface of the extension substantially contacts the convex contact surface of the second endplate and the concave contact surface of the extension directly engages the first and second arcuate slots of the second endplate. The implant is configured for implantation into the intervertebral space by a transforaminal approach.

BRIEF DESCRIPTION OF THE DRAWINGS

The invention will be more readily understood with reference to the embodiments thereof illustrated in the attached figures, in which:

FIGS. 23 and 24 illustrate the present invention according to the embodiment illustrated in FIG. 23.

DETAILED DESCRIPTION OF THE PREFERRED EMBODIMENTS

Figure 1:
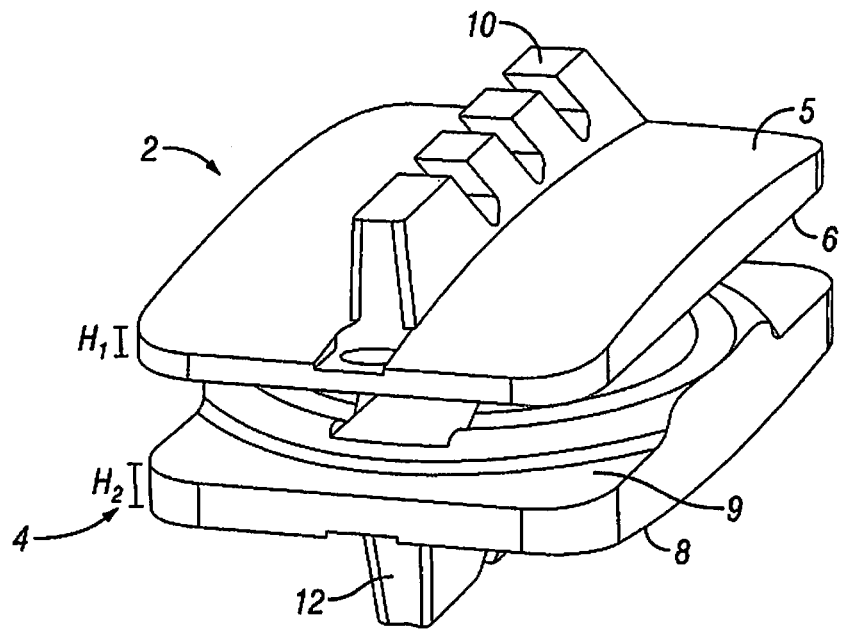
FIG. 1 is an illustration of an embodiment of a prosthetic disc design of the present invention.

Embodiments of the invention will now be described. The following detailed description of the invention is not intended to be illustrative of all embodiments. In describing embodiments of the present invention, specific terminology is employed for the sake of clarity. However, the invention is not intended to be limited to the specific terminology so selected. It is to be understood that each specific element includes all technical equivalents that operate in a similar manner to accomplish a similar purpose.

The present invention relates generally to a prosthetic spinal disc for replacing a damaged disc between two vertebrae of a spine. The present invention also relates to a method for implanting a prosthetic spinal disc via a transforaminal implantation. In particular, the present invention encompasses a method for implanting the prosthetic spinal disc via a transforaminal approach. The present invention further contemplates various instruments, aids, and other devices for implanting the various prosthetic disc designs.

There are any number of considerations that must be factored into designs for prosthetic discs. In addition to size and configuration parameters that impact the implantation approach, the ultimate goal of any prosthetic disc design is to treat patients with spine problems. In some instances, the prosthetic disc design is used to restore proper vertebral body spacing. In other instances, the prosthetic disc design is used to provide a means by which the vertebral bodies may move relative to each other, either mimicking natural movement or providing increased movement as compared to other treatments such as intervertebral fusion. Finally, any number of other considerations may impact the design of a prosthetic disc including, but not limited to, increasing stability of the spine and decreasing negative biomechanical effects on neighboring vertebrae due to degenerative disease.

The present invention contemplates the use of fixed and moving instantaneous axis of rotation (IAR) and/or the center of rotation (COR) of one vertebral body with reference to another. The IAR and COR of a healthy vertebral body with respect to another is constantly changing in all planes because of pushing, pulling, and tethering of the segment through its range of motion by the ligaments, annulus, muscles, facets and other portions of the spine.

Past devices have attempted to mimic or partially mimic natural disc movement by including designs that provide for a moving IAR. These designs, however, typically have been achieved in the past at the expense of a loss of stability of the device. Some examples of prosthetic disc designs having a moving IAR are described in U.S. Pat. Nos. 4,759,766, 5,401,269, and 6,414,551. Co-pending application Ser. Nos. 11/246,149, 10/909,210, 10/827,642, and 60/491,271 describe improved disc designs with variable IARs that mimic or partially mimic the natural movement of a health disc.

During a transforaminal implantation the spine is subjected to increase destabilization as a result of the removal of a facet joint. Additionally, disease or other considerations may lead a surgeon to prefer a prosthetic disc design that does not have a moving IAR. Accordingly, some embodiments of the present invention contemplate prosthetic discs with a fixed IAR. Another advantage of the present disc design relates to the incorporation of stops and other mechanical features of the present invention that reduce the wear and stress on the remaining facet and other structural components of the spine. Generally, past prosthetic disc designs incorporating a ball and socket design with fixed IARs have been known to cause damage to facet joints due to anatomical interferences. The present invention contemplates disc designs that reduce the tendency of fixed IAR prosthetic discs to impact structural wear of the spine.

The materials used for different embodiments of the invention will depend to some extent upon the type of surface contact being used as well as the type and extent of wear that may result. Examples of materials that may be used include, but are not limited to, polyethylene (or other elastomeric material) on metal, metal on metal, polyethylene on polyethylene, or ceramic on ceramic. In some embodiments, metal on metal is preferred because there is reduced wear of the prosthetic disc and reduced debris over long-term use. Alternatively, in some embodiments, ceramic on ceramic may be used. In other embodiments, any number of various combinations of materials may be used.

Any prosthetic disc design must consider the type of and range of movements that it will allow. Naturally, the spine is capable of six degrees of freedom (1) compression, (2) distraction, (3) flexion, (4) extension, (5) lateral bending, (6) rotation, (7) linear translation. Disc designs may be unconstrained, critically constrained, or over-constrained. In an unconstrained device, the range of motion of a prosthetic disc is not limited by any mechanical limits of the prosthetic disc. In an under-constrained device, the prosthetic disc's range of movement is limited to movements outside of the naturally occurring range of movement allowed or permitted by a natural healthy disc. In a critically constrained device, motion is allowed within the physiologic range but limited beyond. An over-constrained device imposes limits on the natural movement. Unconstrained designs of the present invention utilize the various components of the vertebral spine, including muscles, ligaments, facet joints, and other elements of the body to limit the movement of the components of the prosthetic discs. In constrained designs, mechanical stops may be provided to limit the range of movement of the components of the prosthetic disc. The stops may be designed to limit one, two, or more of the various types of movements capable by the prosthetic discs or the natural disc. The present invention contemplates prosthetic disc designs allowing for various degrees of movement, although in some instances, preferred embodiments are constrained in the degree of freedom to limit structural wear of the spine. In alternate preferred embodiments, the design of prosthetic discs of the present invention are constrained to limit the structural wear on a remaining facet.

The articulating surfaces of the prosthetic discs of the present invention may be comprised of a convex and concave surface. In this embodiment of the present invention, the prosthetic disc may allow for axial rotation, radial rotation, extension, flexion, and bending of the spine. In some designs, the articulating surfaces may allow for translation of a vertebral segment relative to another. In the prosthetic disc embodiments of the present invention, the articulating surfaces of the prosthetic disc may be designed to allow for translation in one, two, or more than two directions.

Prosthetic discs of the present invention for use in a transforaminal approach may be comprised of two components: a top piece (also referred to as a top endplate) and a bottom piece (also referred to as a bottom endplate). While for convenience's sake, the designs of the present invention will be described as top and bottom, or superior and inferior, it should be understood that any features associated with one endplate or piece could likewise be associated with the other endplate or piece. Similarly, while the articulating surfaces of the present invention may be described in one particular manner, i.e. with the top piece made of a convex surface and the bottom piece made of a matching concave surface, one in the art would understand that the type of the articulating surface of any particular endplate, whether the top or bottom, is not important.

Each endplate of the prosthetic disc of the present invention has an inner and outer surface. The outer surface of an endplate of the prosthetic disc is designed to interact or contact a vertebral body segment. The inner surface of an endplate is designed with an articulating surface. The articulating surfaces of the present invention are of a ball and socket design, which allow the inner surfaces of the endplates to articulate with respect to each other. The outer surface of an endplate may be designed to conform to the surface of the vertebral body to which the endplate attaches. Accordingly the outer surface may have a particular shape to coincide with the shape of a vertebral body. Alternatively, the outer surface of an endplate may be curved to conform to the contacting surface of a vertebral body. Alternatively, the outer surface of the endplate may have a keel, nails, spikes, or other structure to contact the vertebral body surface. Alternatively, the outer surface of the endplate may have bores through which fasteners may be placed to anchor the endplate to the contacting vertebral body. In some embodiment the outer surface of an endplate may contain one or more of the features described above.

In addition to providing an endplate surface geometry or configuration that may promote bony in-growth to hold the interfacing surfaces together securely over the long term, these configurations also may help provide short term fixation of the endplate to the vertebral body. For example, a keel may have a wedge shape so that the width of a first end of the keel near the endplate is narrower than the width of the distal end. Once installed, the inverted wedge of the keel helps prevent separation of the endplate from the vertebral body at least until bony in-growth can more securely hold the endplate in place.

To help accelerate and to further promote bony in-growth at the interface between the vertebral body and the end plate, the end plate may be coated with an osteoconductive material and/or have a porous or macrotexture surface. For example, the end plate may be treated with a coating that promotes bone growth. Examples of such coatings include, without limitation, hydroxyl appetite coatings, titanium plasma sprays, sintered beads, or titanium porous coatings.

FIG. 1 is an illustration of an embodiment of a prosthetic disc of the present invention. With reference to FIG. 1, the prosthetic disc has a top endplate 2 and a bottom endplate 4. Top endplate 2 has an outer surface 5 and an inner surface 6. Bottom endplate 4 has an outer surface 8 and an inner surface 9. The prosthetic disc of FIG. 1 may be inserted into the intervertebral space in a patient. When inserted, outer surface 5 of top endplate 2 contacts a first vertebral body (not shown). Similarly, outer surface 8 of bottom endplate 4 contacts a second vertebral body (not shown). As can be seen in FIG. 1, both the top endplate 2 and bottom endplate 4 have raised keels 10 and 12. As can be seen in FIG. 1, the top endplate 2 has a height H1. Likewise, bottom endplate 4 has a height H2. The exact height of the top endplate 2 and bottom endplate 4 may vary from design to design depending on any number of considerations including for example the desired disc height in a patient or the amount of space available for implantation of the device.

In one embodiment of the present invention, the surgeon is provided a kit with endplates of prosthetic disc designs. The kit may have, for example, one bottom endplate with a set height and various top endplates with different heights. Accordingly, the surgeon may select a top endplate for implantation with the bottom endplate such that the overall height of the prosthetic disc after implantation restores the height of a natural healthy disc. One advantage of providing a kit with more than one top endplate of various heights, is that it allows the surgeon to customize the prosthetic disc with respect to height during surgery. In addition, the surgeon may also test fit various top endplates during surgery. If the disc height does not appear to be desirable, the surgeon may simply substitute the top endplate for another one in the kit, and hence, make adjustments to the prosthetic disc during surgery. Of course, one of skill in the art would understand that kits may be provided where the top endplate has a fixed height and multiple bottom endplates with various heights are provided. Alternatively, the kit may have multiple top and bottom endplates which may have different heights.

Figure 2:
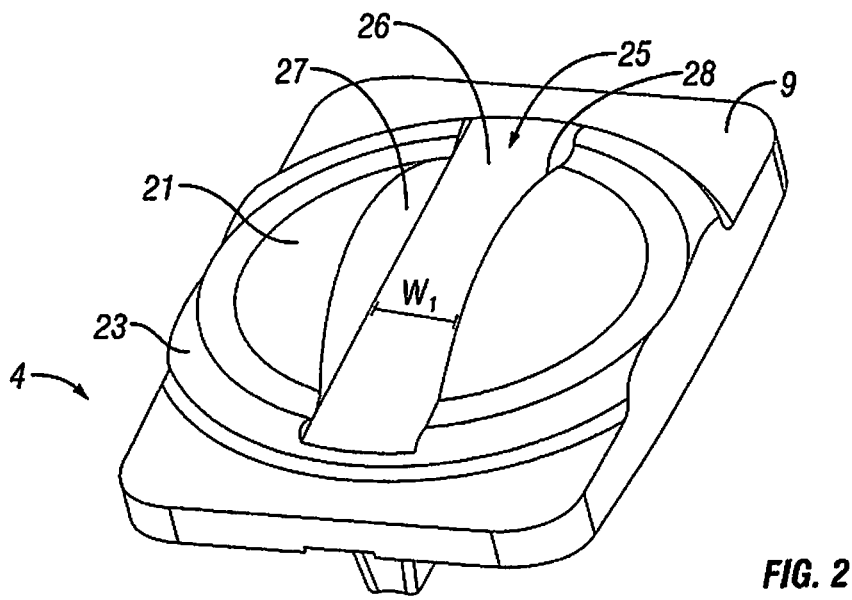
FIG. 2 is an illustration of a bottom endplate of a prosthetic disc design of the present invention.

With reference to FIG. 2, prosthetic disc designs of the present invention generally have endplates made with articulating surface. With continuing reference to FIG. 1 and FIG. 2, bottom endplate 4 may have a partially spherical contact surface 21. Partially spherical contact surface 21 may be convex and extend above inner surface 9 of bottom endplate 4. Partially spherical contact surface 21 may be dimensioned to provide a sufficient area over which a top endplate (not shown) may contact. As can be seen in FIG. 2, partially spherical contact surface 21 is partially surrounded by a rim 23, which creates a transition zone between partially spherical contact surface 21 and inner surface 9 of bottom endplate 4.

FIG. 2 further shows one part of a two-part mechanical stop according to one embodiment of the present invention. As seen if FIG. 2, partially spherical contact surface 21 of bottom endplate 4 has a channel 25 extending through the convex partially spherical contact surface 21. Channel 25 has a bottom wall 26 and two side walls 27 and 28. Bottom wall 26 of channel 25 is substantially flat or parallel with interior surface 9 of bottom endplate 4. In alternative embodiments, however, bottom wall 26 of channel 25 may be convex or concave.

Figure 3:
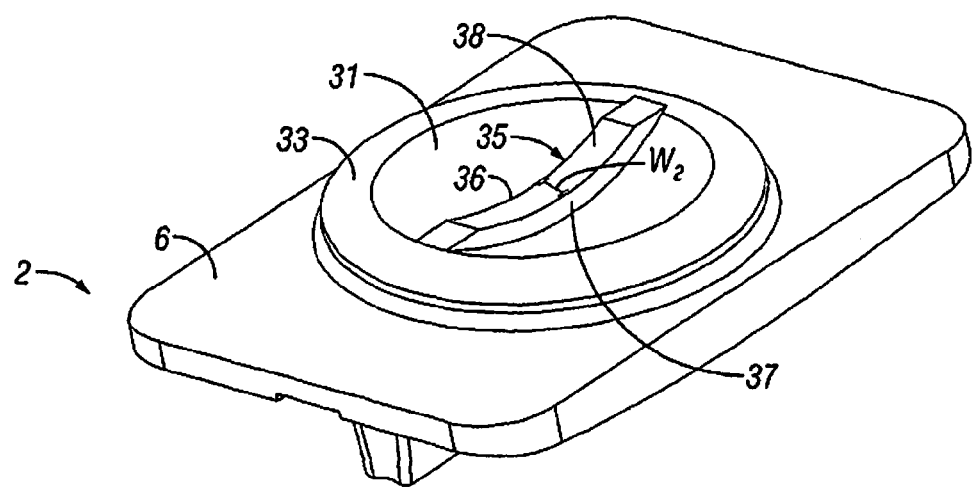
FIG. 3 is an illustration of a top endplate of a prosthetic disc design of the present invention.

FIG. 3 is an illustration of a top endplate of a prosthetic disc according to one embodiment of the present invention. Top endplate 2 has a partially spherical contact surface 31 that is concave. Partially spherical contact surface 31 may be dimensioned to provide a sufficient area over which a bottom endplate (not shown) may contact. Accordingly and with reference to FIG. 2 and FIG. 3, partially spherical contact surface 31 of top endplate 2 and partially spherical contact surface 21 of bottom endplate 4 are substantially of similar dimension and shape such that when the prosthetic disc is assembled, contact surfaces 21 and 31 mate over an area of each respective surface to create articulating surfaces. The articulating surfaces of this ball and socket type design impart the degrees of movement between top endplate 2 and bottom endplate 4.

As seen in FIG. 3, partially spherical contact surface 31 is at least partially surrounded by rim 33. Rim 33 defines the outer circumference of partially spherical contact surface 31 and creates a transition zone between partially spherical contact surface 31 and inner surface 6 of top endplate 2. As further seen in FIG. 3, partially spherical contact surface 31 contains a raised portion or protrusion 35. Protrusion 35 generally comprises the second part of a two-part mechanical stop. Protrusion 35 runs radially from one point along the outer circumference of partially spherical contact surface 31 to its opposite point through the center of partially spherical contact surface 31. Protrusion 35 extends above partially spherical contact surface 31 and has two side walls 36 and 37 and a bottom wall 38. In FIG. 3, the protrusion is shown with a concave bottom side wall although in alternative designs, bottom wall 38 may be convex or parallel to interior surface 6 of top endplate 2.

Whatever the particular design, the mechanical stops are intended to provide constraints on the degrees of movement of the prosthetic disc, i.e., the degrees of movement allowed by the articulating surfaces of the contacting endplates. With continuing reference to FIGS. 2 and 3, channel 25 and protrusion 35 are designed to limit rotation of the prosthetic disc. In this embodiment of the present invention, channel 25 has a width W1. Protrusion 35 is designed with a width, W2, that is less than W1. The particular widths, i.e. W1 and W2 may vary, although their dimensions will determine the amount of rotation allowed. When assembled, partially spherical contact surfaces 21 and 31 are mated or in contact and protrusion 35 lies or fits within channel 25. Upon rotation, side walls 36 and 37 of protrusion 35 may contact side walls 27 and 28 of channel 25, hence limiting movement. As one of ordinary skill in the art would understand, the respective widths of protrusion 35 and channel 25 will determine the amount of rotation allowed.

Prosthetic disc designs of the present invention may further contain additional mechanical stops to control or limit movement in other degrees of freedom. For example and with continuing reference to FIGS. 2 and 3, interior surfaces 31 and 21 of top and bottom endplates 2 and 4, respectively, may contain mechanical stops to limit lateral bending, flexion, and extension. As seen in FIGS. 2 and 3, rims 33 and 23 of top and bottom endplates 2 and 4, respectively, may be used to mechanically limit the lateral bending, flexion, and extension. In this embodiment, rims 33 and 23 of top and bottom endplates 2 and 4, respectively, are dimensioned and sized such that during flexion, extension, and/or lateral bending, rim 33 of the top endplate 2 and rim 23 of bottom endplate 4 may contact each other and prevent the articulating surfaces, i.e. partially spherical contact surface 31 of top endplate 2 and partially spherical contact surface 21 of bottom endplate 4, from further articulation.

Figure 4:
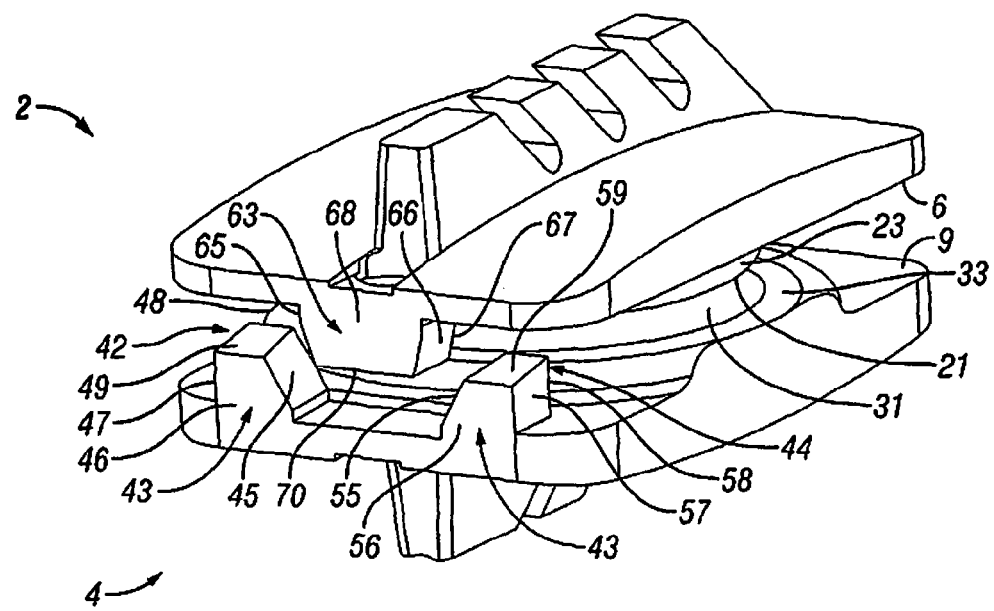
FIG. 4 is an illustration of an embodiment of a prosthetic disc design of the present invention.

In an alternate embodiment of the present invention, alternative mechanical stops are provided. With reference to FIG. 4, a prosthetic disc design is illustrated with mechanical stops to limit rotation of the respective articulating surfaces. As seen in FIG. 4, partially spherical contact surface 21 of bottom endplate 4 and partially spherical contact surface 31 of top endplate 2 are in contact and do not contain any additional channels or protrusions as in previous designs. Instead, mechanical stops are formed on the interior surfaces 6 and 9 of the top endplate 2 and bottom endplate 4.

As seen in FIG. 4, interior surface 9 of bottom endplate 4 contains a first part 43 of a two-part rotational stop. In this particular embodiment, the rotational stop is located on the posterior portion of the prosthetic disc. A first part 43 of the rotational stop is located on the interior surface 9 of lower endplate 4. First part 43 of the rotational stop is made of a first and second protrusion 42 and 44, respectively, that extends from the interior surface 9 of bottom endplate 4. Protrusion 44 has five walls, four side walls 45, 46, 47, 48 and one top wall 49. Similarly, protrusion 42 has five walls, four side walls 55, 56, 57, 58 and a top wall 59. In this particular embodiment of the prosthetic disc design, side walls 45 and 55 have angled surfaces as seen in FIG. 4. The second part of the rotational stop is located on the interior surface 6 of top endplate 2. This part of the rotational stop is a protrusion that extends below the interior surface 6 of top endplate 2. Top endplate protrusion 63 has five walls, including four side walls 65, 67, 68, 69 and one bottom wall 70. In this particular embodiment of the prosthetic disc design, side walls 65 and 66 have angled surfaces as seen in FIG. 4.

With continuing reference to FIG. 4, the first and second protrusions 42 and 44 of bottom endplate 4 and protrusion 63 of top endplate 2 are not in contact when the prosthetic disc is assembled and in its neutral position (shown in FIG. 4). During rotational movement, however, protrusion 63 of top endplate 2 will contact one of the first or second protrusions 42 or 44 of bottom endplate 4. For example, in one direction of rotation, side wall 65 of protrusion 63 of top endplate 2 will contact side wall 45 of first protrusion 42 of bottom endplate 4, thus, limiting the movement or the articulating surfaces of the top and bottom endplates 2 and 4. As seen in FIG. 4, angled side walls 45, 55 and 65, 67 may cause the endplates to move as in flexion. Accordingly, this design provides a softer or more cushioned rotational stop than would be encountered if the side walls were perpendicular to their respective interior surfaces. In alternative embodiments, the angles formed between the side walls and interior surfaces may be acute, in which case the rotational stops might additionally serve to create the opposite movement described above, namely, extension. As one of skill in the art would understand, the placement of the rotational stops and angles of the side walls may be varied to achieve various results and degrees of movement.

Preferably, the height of first and second protrusions 42 and 44 of bottom endplate 4 are sized, in conjunction with the height of protrusion 63 of top endplate 2, such that the upper walls 49 and 59 of first and second protrusions 42 and 44 of bottom endplate 4 do not interfere or contact interior surface 6 of upper endplate 2 during flexion, extension, or lateral bending. Rather, rims 23 and 33 of upper endplate 2 and lower endplate 4 act to limit movement in those directions. Similarly, protrusion 63 of top endplate 2 is sized such that bottom wall 69 does not come into contact with interior surface 9 of bottom endplate 4. The height of the rotational stop protrusions 42, 44, 63 may be larger or smaller depending on the amount of flexion, extension, and lateral bending allowed by the rims on the interior surfaces of the top and bottom endplate as discussed above. Alternatively, in embodiments where rims are not provided as mechanical stops for flexion, extension, and lateral bending, the heights of the protrusions may be sized such that top walls 49 and 59 and bottom wall 69 do come into contact with the interior surfaces of the top and bottom endplate, thus also serving as mechanical stops for flexion, extension, and lateral bending. Of course, one of skill in the art would understand that to limit all three types of movement (in addition to the rotational limitation) in a prosthetic disc design without rims, the design may require an additional set of protrusions located at an anterior portion of the prosthetic disc.

Figure 5:
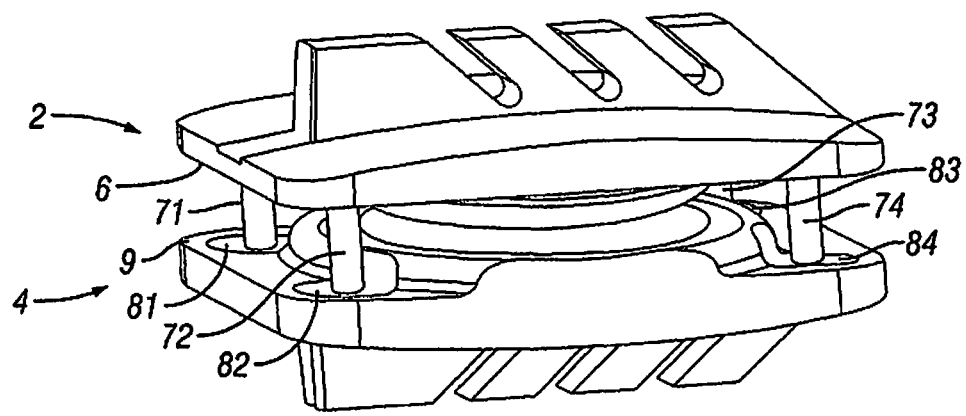
FIG. 5 is an illustration of an embodiment of a prosthetic disc design of the present invention.

FIG. 5 is an illustration of another embodiment of a prosthetic disc design with an alternative mechanical stop design. As seen in FIG. 5, rotational stops may be provided located on the interior surface 6 of upper endplate 2. In this embodiment, four cylindrical shaped pins 71, 72, 73, 74 are located on the four corners of interior surface 6 of top endplate 2. Bottom endplate is formed with holes 81, 82, 83, 84 on interior surface 9 of bottom endplate 4 directly below cylindrical shaped pins 71, 72, 73, 74, respectively. In the prosthetic disc's neutral position, cylindrical pins 71-74 extend at least partly within the cavities created by holes 81-84, respectively. Accordingly, during rotational movement the exterior surfaces of pins 71-74 contact the interior surfaces of holes 81-84 limiting movement. In some designs, holes 81-84 extend entirely through bottom endplate 4. In alternative designs, holes 81-84 may be blind holes, i.e. where holes 81-84 do not extend through bottom endplate 4.

As would be understood by one of skill in the art, holes 81-84 are sized in conjunction with pins 71-74, to provide for the freedom of movement desired. Similarly, where holes 81-84 are blind holes, in some designs the depth of holes 81-84 and the length of pins 71-74 may be dimensioned such that pins 71-74 contact the bottom portion of their respective holes 81-84 during flexion, extension, and/or lateral bending. This additional stop mechanism may work in conjunction with the rim design previously described or may substitute the rims and be the primary mechanical stop to limit or constrain flexion, extension, and/or lateral bending. In alternative embodiments, only one pin and one hole may be provided. In alternative embodiments, more than one hole and pin is provided. Furthermore, it would be understood by one of skill in the art that the pins and holes need not be cylindrical in shape but may also take various shapes yet still serve as rotational stops. Similarly, one of skill in the art would understand that of the various mechanical stops described, any number of variations and combinations may be employed to limit movement of the articulating surfaces of the prosthetic disc designs.

In an embodiment of the present invention the prosthetic disc design is rotationally constrained and the endplates are allowed to rotate 1° in either direction from its neutral position. In alternative embodiments the prosthetic disc design is rotationally constrained and the endplates are allowed to rotate 10° or more in either direction from its neutral position. In some embodiments of the present invention, the prosthetic disc design may be unconstrained in one, two, or more than two degrees of freedom. In some embodiments of the present invention, the prosthetic disc design may be constrained in one, two, or more than two degrees of freedom.

In one embodiment of the present invention, the upper and lower portions of a disc assembly may be configured with a keel that can engage with or contact a neighboring vertebral body. One advantage of providing a keel is that it may be used to guide the assembly into position during insertion into a treated area of the spine. For example, a channel or groove may be cut out of a vertebral body to facilitate insertion of a keel. Then, a physician may insert the assembly into the vertebral body so that the keel slides in the groove or channel. The keel and grove may be substantially linear or straight, or alternatively, may be curved or arched so that the assembly rotates and slides into position. The ridges or keels and corresponding channels or grooves also may be straight or curved to match the desired insertion path of the assembly. The grooves or channels formed in a vertebral body may help achieve the proper orientation and distance of the assemblies and provide for a secure anchoring of the endplate or endplates.

The cross-sectional profile of the keel may have different shapes. For instance, the cross-sectional profile of the keel may have the shape of a wedge, a truncated wedge, a rectangle, or a square. The channel or groove may be cut to have a cross-sectional profile corresponding approximately to the shape of the keel. One advantage of the keel having a truncated wedge cross-section is that a similarly shaped channel or groove may ensure that the keel engages with the bony surface. This configuration may also provide increased resistance to expulsion of the disc assembly.

Figure 6:
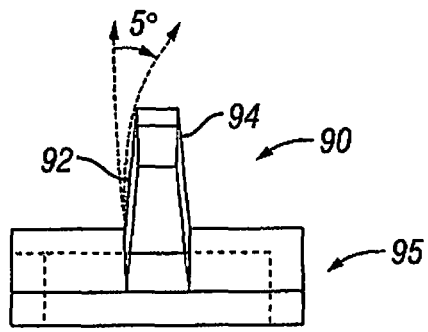
FIG. 6 is an illustration of a keel of a prosthetic disc design of the present invention.

In one embodiment, the cross-section of a ridge or keel may be triangular or have a truncated triangular shape. For example, as shown in FIG. 6, keel 90 is of a truncated triangular shape. The height of keel 90 may vary, but may be configured with sloped sides 92 and 94, as shown in FIG. 6, of about 5° from the longitudinal plane. The height of keel 90 may vary, but in general is designed to provide sufficient contact area once inserted in the vertebral body to anchor endplate 95. The keel may be sized such that any groove or channel cut into the vertebral body to accommodate the keel does not substantially impact the structural integrity of the vertebral body.

The use of one or more keels may also increase bone to implant surface contact, thereby decreasing the likelihood that the assembly will shift or move about of position. In one embodiment, the increase in surface contact may be about 5% or more, which in another embodiment the increase may be about 15% or more.

Over time, it is believed that the stability of the disc assembly in the treated area will further increase as bone growth engages with outer surfaces of the disc assembly. To facilitate this growth and increased stability, all or part of the surfaces of the disc assembly that engages or otherwise contacts bone may be treated to promote bony in-growth. For instance, titanium plasma may be provided on the keel or other portions of the assembly to provide a matrix for bone growth. In addition, the keel may be configured with notches, slots, or openings formed along its length. As bone grows into these openings, the disc assembly will become more securely anchored in place.

Figure 7:
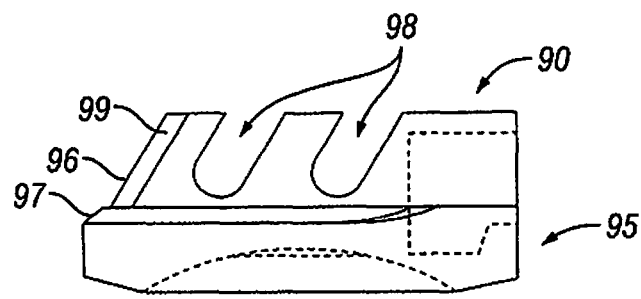
FIG. 7 is an illustration of a keel of a prosthetic disc design of the present invention.

As a disc assembly is first inserted into a treated area, it may need to be repositioned, rotated or otherwise moved. For instance, repositioning the disc assembly may be needed so that the keel can properly engage with the channel or groove. As shown in FIG. 7, keel 90 of endplate 95 has an angled first leading edge 96. Additionally, endplate 95 may be configured with a second leading edge 97 that does not contain part of keel 90. Thus, in one embodiment the assembly can be partially inserted into the treated area without keel 90 engaging with or contacting the vertebral body. In one embodiment, the length of second leading edge 97 is from about 1 mm to about 10 mm, while in another embodiment second leading edge 97 is from about 2 mm to about 5 mm. Alternatively, the length of second leading edge 97 may be from about 1% to about 20% of the length of the endplate 95 on which it is disposed, or may be from about 2% to about 10%. The length of the endplate 95 may be determined by measuring the longitudinal central axis of the portion or endplate on which second leading edge 97 is disposed.

In addition, referring again to FIG. 7, keel 90 may have first leading edge 96 that is sloped or gradually increases in height. As seen in FIG. 7, first leading edge 96 is sloped. Providing a ramped first leading edge 96 may aid in aligning and inserting keel 90 into a groove or channel formed in a vertebral body.

As mentioned previously, the keel of a disc assembly may be configured to promote or permit bony in-growth that may help hold the disc assembly in place more securely. FIG. 7 further illustrates an embodiment of keel 90 having a plurality of slots or cuts 98 formed in it. In FIG. 7, slots 98 may extend at an angle, such as from about 50 to about 40° off from a vertical direction, and more preferably from about 10° to about 30° Keel 90 may have two or more, or even three or more slots or cuts. One skilled in the art would appreciate that other configurations may also be used to promote bony in-growth that might help further secure the disc assembly in place. For instance, the keel may have holes or apertures drilled into it, longitudinal or horizontal slots may be formed, and the sidewalls of the keel may be textured with one or more grooves or channels that does not extend fully through the keel to the opposing sidewall.

In addition, the face of the keel that is first inserted into a groove or channel may have a taper or chamfer. One potential advantage of configuring a keel with a taper or chamfer on its face is that it may assist in aligning the keel with the opening of the channel or groove. In addition, a chamfered or tapered face may help reduce drag forces and undesired cutting or gouging of the channel or groove as the keel is pushed toward its final position. As seen in FIG. 7, the face of keel 90 is configured with a chamfer 99 to aid in the insertion of the prosthetic disc.

Figure 8:
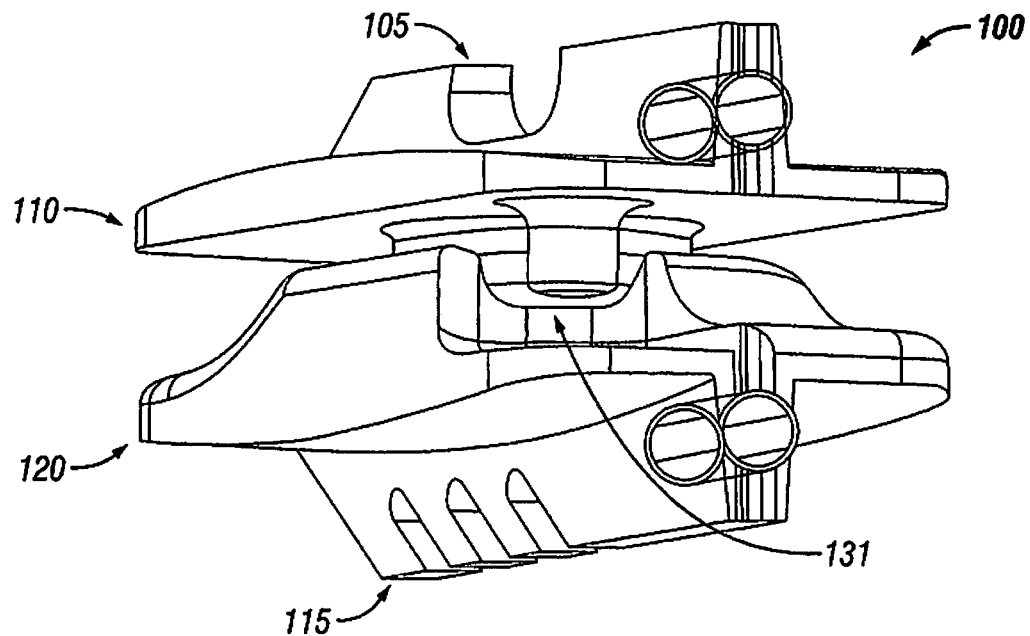
FIG. 8 is a perspective view of another embodiment of the present invention.

In an alternate embodiment of the present invention, different prosthetic disc designs may be provided. With reference to FIG. 8, an alternate embodiment of the present invention is provided. As seen in FIG. 8, a prosthetic disc 100 is provided having an upper endplate 110 and lower endplate 120. Upper endplate 110 may be configured with a keel 105, as discussed previously, to guide the endplate during implantation and increase contact area between the upper endplate 110 and the upper vertebral body (not shown). Similarly, lower endplate may be configured with a keel 115, to guide the endplate during implantation and increase the contact area between lower endplate 120 and the lower vertebral body (not shown).

Figure 9:
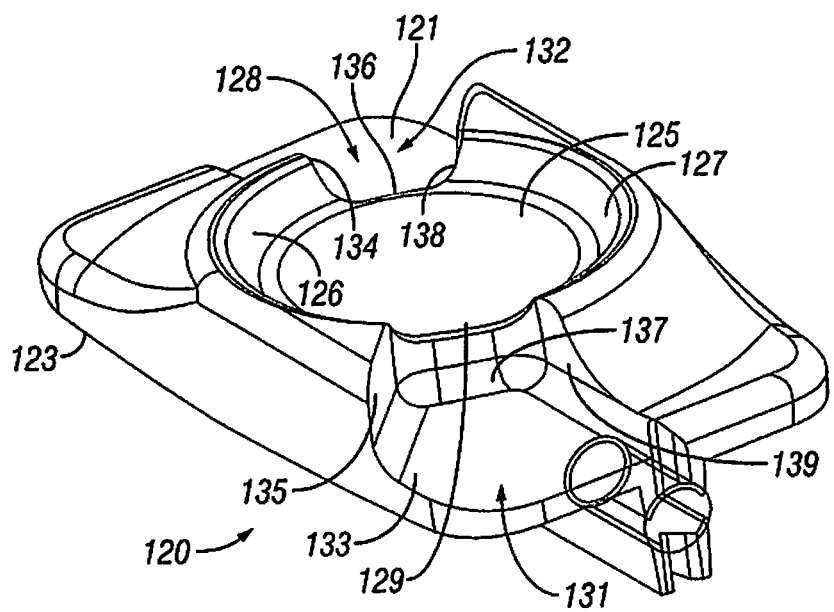
FIG. 9 is a perspective view of an endplate of the embodiment of FIG. 8.
Figure 10:
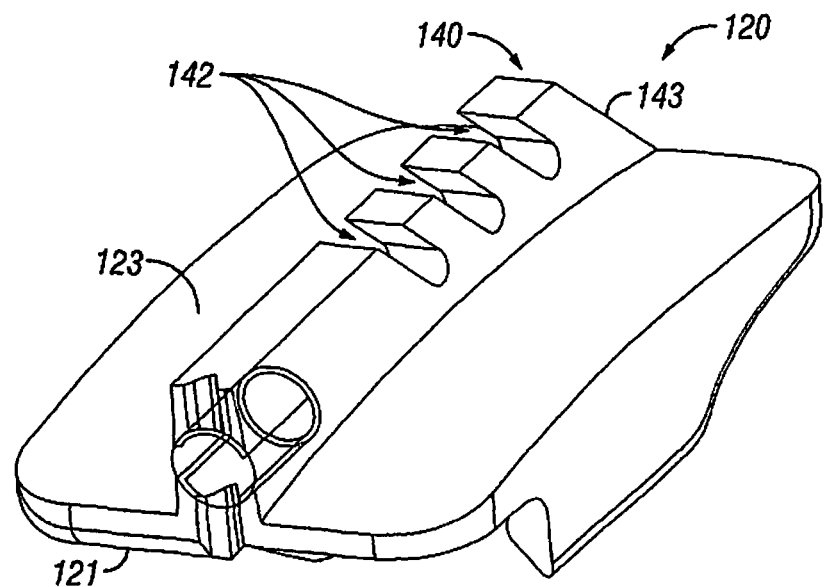
FIG. 10 is a perspective view of an endplate of the embodiment of FIG. 8.

With continuing reference to FIG. 8, FIGS. 9 and 10 illustrate the lower endplate. In FIG. 9, the lower endplate 120 is illustrated showing its superior surface 121, whereas in FIG. 10, the lower endplate is illustrated showing its inferior surface 123, i.e. the surface which contacts the lower vertebral body. As seen in FIG. 9, the lower endplate is configured with a partially spherical surface 125, which is concave and provides a seating surface configured to contact with the convex, partially spherical surface of the upper endplate (described below). Disposed about concave partially spherical surface 125 of lower endplate 120 is a partially conical rim that forms sidewalls 126 and 127 to the concave partially spherical surface 125. Disposed about the perimeter rim of the concave, partially spherical surface 125, are two opposing windows 128 and 129 formed out of, or interrupting, sidewalls 126 and 127.

As seen in FIG. 9, window 129 leads to a cavity 131 that is has an inferior surface 133 and three sidewall surfaces 135, 137, and 139. While partially hidden in FIG. 9, one of skill in the art would understand that window 128 leads to cavity 132, which is similarly formed with sidewall surfaces 134, 136, and 138. Cavities 131 and 132 are recesses formed within lower endplate 120 that are configured to interact with stops on the upper endplate, as described in more detail below.

With reference to FIG. 10, lower endplate 120 is shown having an inferior surface 123 upon which keel 140 is formed. The keel extends generally the length of the lower endplate 123 and is disposed generally along the midline of lower endplate 120. Keel 120 may have notches 142 formed within the keel body to provide areas into which bone may grow, and hence, provide a mechanism for increasing the attachment of lower endplate 123 to the vertebral body. Similarly, keel 140 may be formed with a leading edge 143 that is slanted towards the center of lower endplate 120. This leading edge helps during insertion by providing a favorable contact surface as the prosthetic disc is inserted into the vertebral space.

Figure 11:
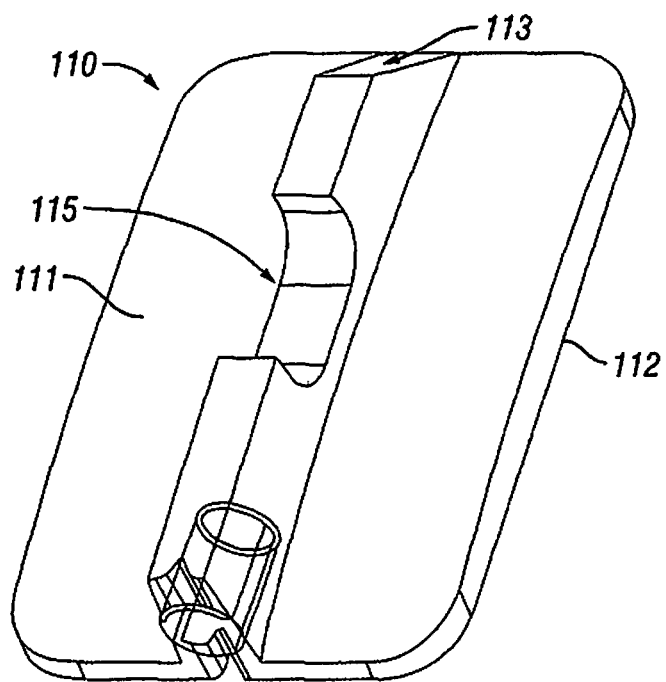
FIG. 11 is a perspective view of an endplate of the embodiment of FIG. 8.
Figure 12:
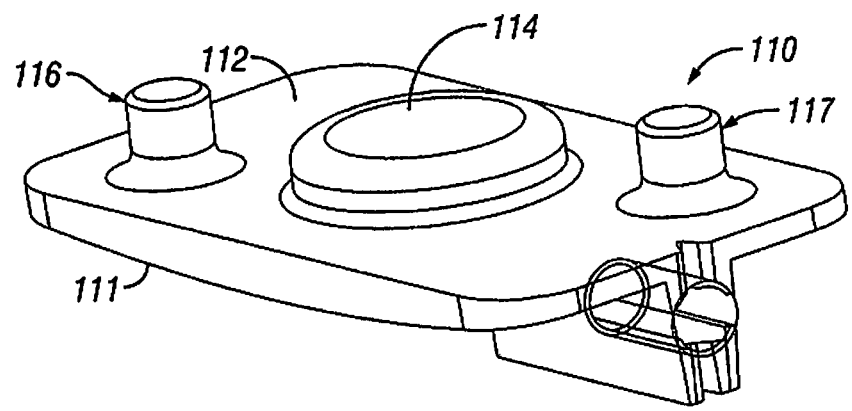
FIG. 12 is a perspective view of an endplate of the embodiment of FIG. 8.

With reference to FIGS. 11 and 12, upper endplate 110 is shown. In FIG. 11, the upper endplate 110 is shown with a view of its superior surface 111, whereas in FIG. 12, upper endplate 110 is shown with a view of its inferior surface 112. As can be seen in FIG. 11, the upper endplate has a keel 113, similarly positioned and configured as keel 140 of lower endplate 120. One difference in this embodiment, however, is that keel 113 of upper endplate 110 may have a window or cut-out 115 formed within keel 113. The cut-out 115 of keel 113 is a cavity disposed generally in the center portion of keel 113. Cut-out 115 is preferably symmetrical and extends along keel 113 in equal directions from the center of the prosthetic disc. As a positioning feature, the cut-out is most effective if the center of cut-out 115 is the same as the center of upper endplate 110 and prosthetic disc 100. In these instances, as one of skill in the art would understand, when the profile of prosthetic disc 100 is viewed in the medial-lateral plane, the center of cut-out 115 corresponds to the center of the prosthetic disc. The positioning feature allows a surgeon to position the prosthetic disc within the intervertebral space, regardless of the angle at which the prosthetic disc was placed. Because the window remains visible in a profile view along a variety of angles, the center of the cut-out can be used to position the prosthetic disc within the vertebral space. In this way, the cut-out provides a way to position the prosthetic disc within the intervertebral space in a consistent and simple manner, which is independent of the angle of insertion. This feature may also be used after implantation of the prosthetic disc during follow up visits to track the position of the prosthetic disc postoperatively.

With reference to FIG. 12, the inferior surface 112 of upper endplate 110 is shown. As seen in FIG. 12, a partially spherical convex surface 114 extends in the inferior direction from the inferior surface 112 of upper endplate 110. Partially spherical convex surface 114 of upper endplate 110 is configured to engage with partially spherical concave surface 125 of lower endplate 120 when the prosthetic disc is assembled. In this manner, the contacting surfaces, i.e. partially spherical concave surface 125 and partially spherical convex surface 114, may articulate with respect to each other. The articulating surfaces provide the relative rotation of the adjacent vertebral bodies, above and below the prosthetic disc. The partially spherical nature of the contacting surfaces provides the fixed IAR and COR previously described above.

As can be further seen in FIG. 12, the inferior surface 112 of upper endplate 110 is configured with two stops 116, 117 that extend downward from the inferior surface 112 of upper endplate 110. In this embodiment, the stops are shaped as truncated cylinders, although in alternate embodiments the stops may take the form of any variety of shapes and configurations. As seen in FIG. 12, the stops are spaced apart from the partially spherical convex surface 114 of upper endplate 110. As further seen in FIG. 8, when upper endplate 110 and lower endplate 120 are assembled, stops 116 and 117 of upper endplate 110 fit within cavities 128 and 129 of lower endplate 120. While FIG. 8 is shown with the prosthetic disc in its neutral position, one of skill in the art would understand, that upon axial rotation of the endplates with respect to each other, the stops would interact with the sidewalls of cavities 131, 132 and limit rotation of the endplates relative to each other. As seen in FIG. 9, sidewall 135 provides a surface against which stop 117 abuts. As further seen in FIG. 9, sidewall 139 is not necessarily configured to provide a contact surface for stop 117. This is so because in this particular design, the remaining facet acts as a limiting mechanism for rotation in that direction. Accordingly, one of skill in the art would understand that depending on the facet removed, this embodiment may be designed in alternative configurations such that a mechanical stop is integrated into the prosthetic disc design to compensate for the removed facet, while relying on the remaining facet to act as a natural stop for rotation in the opposite direction.

As one of skill in the art would understand, the sizes of the cavities and stops may be varied to allow for the range of movement desired. Accordingly, in some instances it may be desirable to limit axial rotation to between about 11 to about 10° In alternative embodiments axial rotation is limited to between about 3° to about 7°, or between about 4° to about 6°, or to between about less than 1° to more than 5.°

Figure 13:
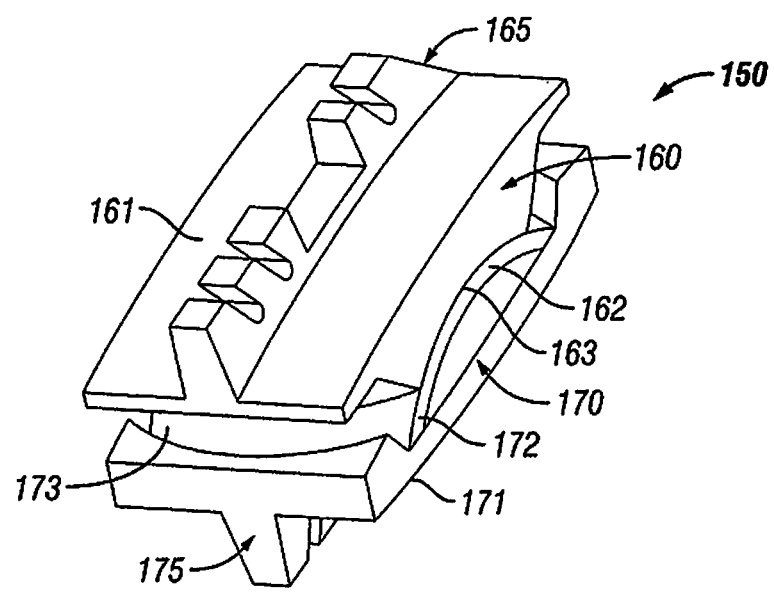
FIG. 13 is a perspective view of an embodiment of the present invention.

In an alternate embodiment, prosthetic disc 150 has an upper endplate 160 and lower endplate 170. With reference to FIG. 13, upper endplate is configured having a superior surface 161 and inferior surface 162. Superior surface 161 of upper endplate 160 is configured with a keel 165, which may contain similar features as previously described. Inferior surface 162 of upper endplate 160 has a partially spherical concave surface 163. With continuing reference to FIG. 13, lower endplate is configured with an inferior surface 171. Inferior surface 171 of lower endplate 170 is configured with a keel 175, which also may contain similar features as previously described. Superior surface 172 of lower endplate 170 has a partially spherical concave surface 173.

Figure 14:
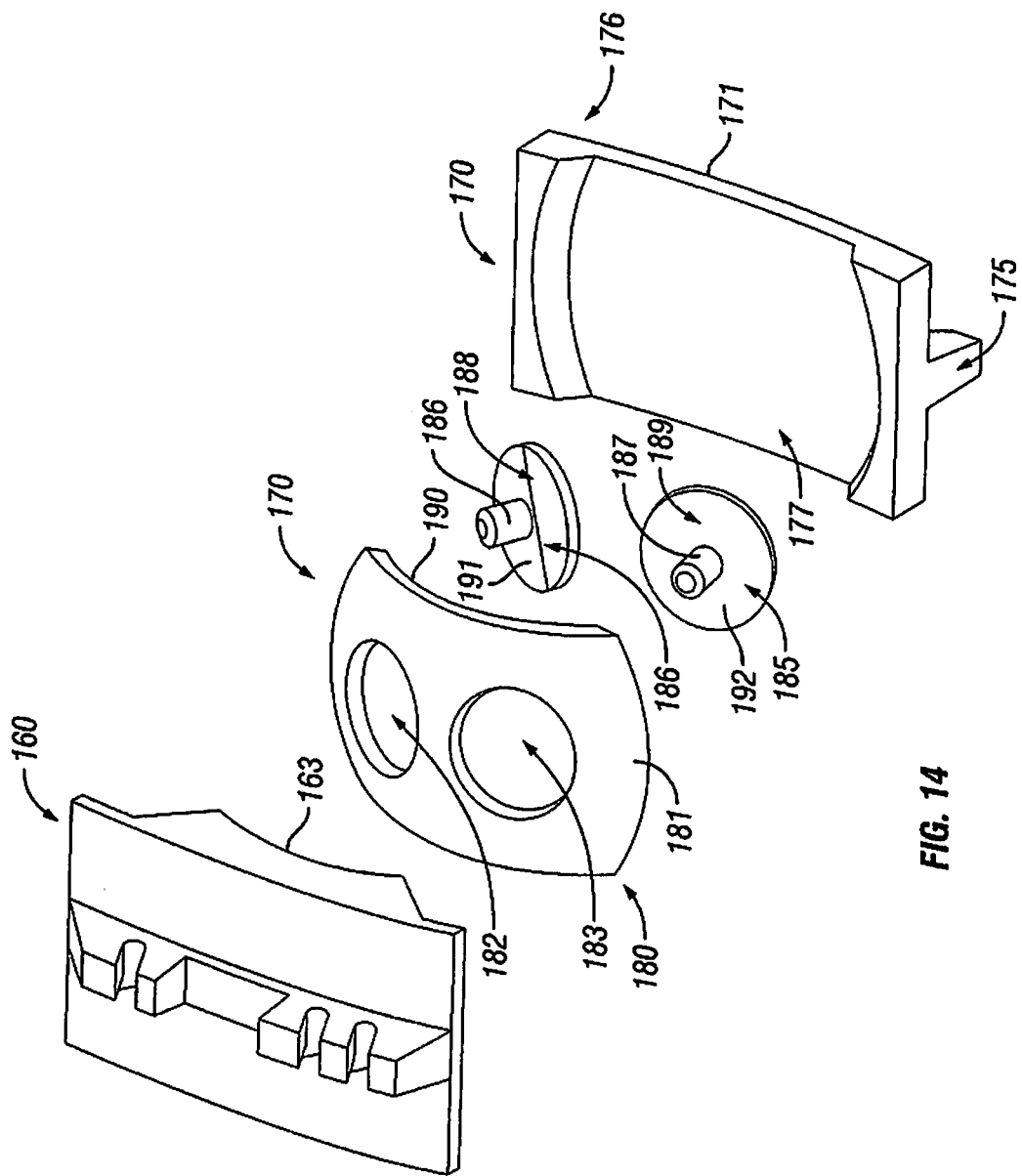
FIG. 14 is an exploded view of the embodiment of FIG. 13.

With continuing reference to FIG. 13, FIG. 14 illustrates an exploded view of the embodiment of FIG. 13. As seen in FIG. 14, lower endplate 170 is constructed from two pieces to from the lower endplate 170. First portion 176 comprises the inferior surface 171 having a keel 175 and superior surface 177 configured to receive a second portion 180. Second portion 180 is a partially spherical wedge having a discreet thickness and curvature. The curvature of partially spherical convex wedge 180 corresponds to the partially spherical concave surface 163 of the inferior surface 162 of upper endplate 160, thus forming a partially spherical convex surface 181. While any number of methods may be used, one non-limiting method of attaching first portion 176 to second portion 180 may be welding. In this example, the lower endplate 170 is formed of a first portion 176 and second portion 180, wherein after attachment of the second portion 180 to the first portion 176 a cavity is formed between the first portion 176 and second portion 180 of lower endplate 170. As seen in FIG. 14, second portion 180 further has two bore holes 182, 183 disposed on its partially spherical convex surface 181.

Stops 185, 186 may be used to limit the articulating between the partially spherical concave surface 163 of upper endplate 160 and the partially spherical convex surface 181 of second portion 180 of lower endplate 170. Stops 182, 183 have two portions, an attaching portion 186, 187 and a washer portion 188, 189, respectively. These portions may be integrally formed as one piece or may be formed as separate pieces. In an embodiment, attaching portion 186 is shaped as a cylindrical rod as seen in FIG. 14. Attaching portion 186 is configured to attach to upper endplate 160 on one end and attach to washer portion 188 on the other end. The attachment may be by any number of different means including welding, fixation compounds, threaded attachments or others. When assembled, attaching portion 186 is fixedly attached to the partially spherical concave surface 163 of upper endplate 160. Additionally, washer portion 188 is fixedly attached to attaching portion 186 after upper endplate 160 and lower endplate 170 have been assembled, i.e., partially spherical concave surface 181 and partially spherical convex surface 163 are in contact. In this embodiment, attaching member 186 is attached to the upper endplate 160 such that when the prosthetic disc is assembled, attaching members 186, 187 pass through bore holes 182, 183 respectively. Washer members 188, 189 are configured to contact or abut the lower surface 190 of partially spherical wedge 180.

Washer members 188, 189 are also configured such that the upper surfaces 191, 192 of washer members 188, 189 are sized such that washer members 188, 189 will not pass through bore holes 182, 183. Accordingly as one of ordinary skill in the art would understand, when assembled, partially spherical convex surface 181 and partially spherical concave surface 163 may articulate with respect to each other but will be limited by the interaction between the solid perimeters of bore holes 182, 183 and their interaction with attaching portions 186, 187 of stops 186, 185 respectively. Similarly, washer portions 188, 189 act to limit separation of the upper endplate 160 and lower endplate 170.

As should be apparent from the foregoing description the size of the attaching members 186, 187 and/or the bore holes 182, 183 may be adjusted to increase or decrease the amount of articulating that may be experienced between the partially spherical surfaces 163, 181. Additionally, one of ordinary skill in the art would understand that the configuration of bore holes 182, 183 and/or attaching members 186, 187 may differ, which would impact the degrees of freedom of the articulating surfaces 163, 181. For example, where the bore holes are dimensioned to be generally of elliptical shape, the articulating surfaces may rotate in greater amounts along the long access of the elliptical bore hole as compared to the short axis. The present invention contemplates the use of differently sized bore holes and/or attaching members to create prosthetic discs with customized degrees of rotation along any number of parameters, whether it be increased flexion/extension, increased lateral bending, etc.

Figure 15:
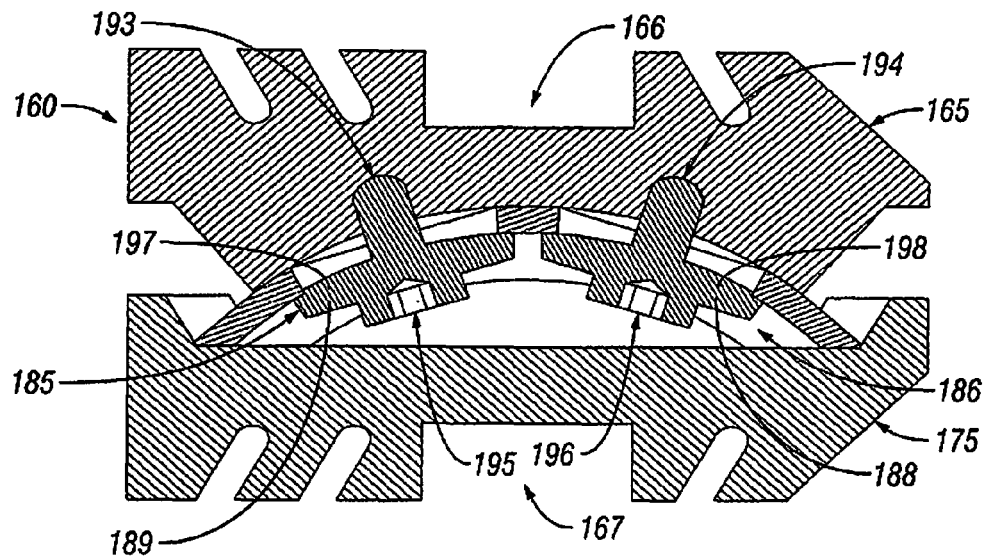
FIG. 15 is a cross sectional view of the embodiment of FIG. 13.

With reference to FIG. 15, a cross sectional view of an assembled prosthetic disc of the embodiment of FIGS. 13 and 14 is shown. As seen in FIG. 15, stops 185, 186 may be formed with a threaded end on stops 185, 186. Similarly, upper endplate 160 may be formed with threaded cavities 193, 194 into which stops 185, 186 may be inserted. Stops 185, 186 may be configured with engagement areas 195, 196 to drive stops 185, 186 into threaded cavities 193, 194 of upper endplate 160. In this particular embodiment, engagement areas 195, 196 take the form of hexagonal heads for a hexagonal driver (not shown). As also seen in FIG. 15, upper surfaces 197, 198 of washers 188, 189 of stops 185, 186 may correspond to the curvature of lower surface 190 of wedge 181 of lower endplate 170. In FIG. 15, one may also see how keels 165, 175 are formed with windows 166, 167 to aid positioning of the prosthetic disc as described previously.

Figure 16:
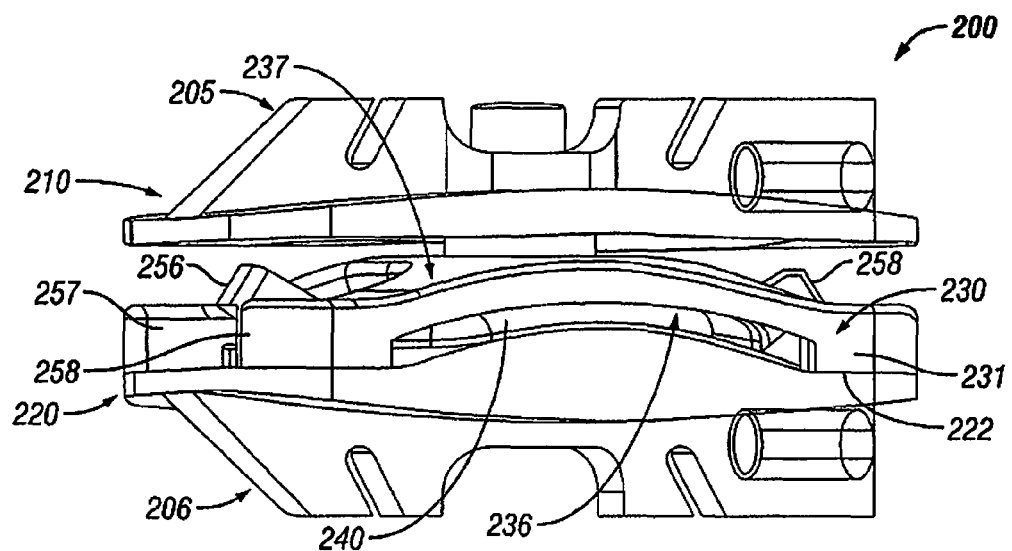
FIG. 16 is a perspective view of an embodiment of the present invention.

With reference to FIG. 16, an alternate embodiment of a prosthetic disc is shown. Prosthetic disc 200 may be configured with upper endplate 210 having a keel 205 with features similar to those described previously. Bottom endplate 220 may similarly be configured with a keel 206 having features as described above.

Figure 17:
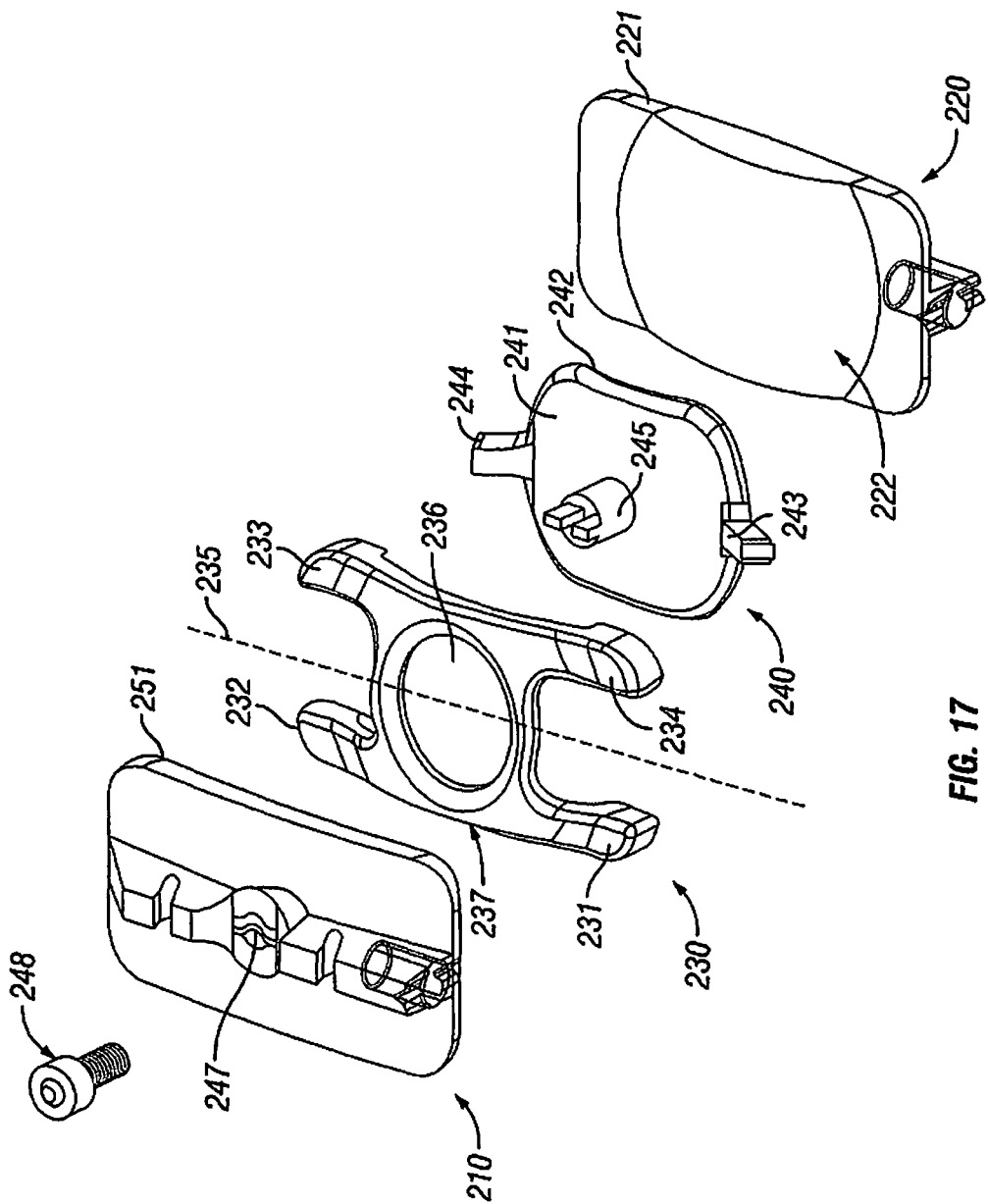
FIG. 17 is an exploded view of the embodiment of FIG. 16.

Referring to FIG. 17, bottom endplate 220 may have a lower surface 221 and upper surface 222. As seen in FIG. 17, upper surface 222 of bottom endplate 220 may be a partially spherical convex surface. Interposed between top endplate 210 and bottom endplate 220 are two intermediate portions 230, 240. First intermediate portion 230 may have a generally circular portion from which four arms 231, 232, 233, 234 may extend tangentially along the latitudinal axis 235 of the prosthetic disc. First intermediate portion 230 may be foamed with a bore hole 236 disposed centrally as shown in FIG. 16. Arms 231-234 are designed to attached to lower endplate 220 as described in more detail below.

Figure 18:
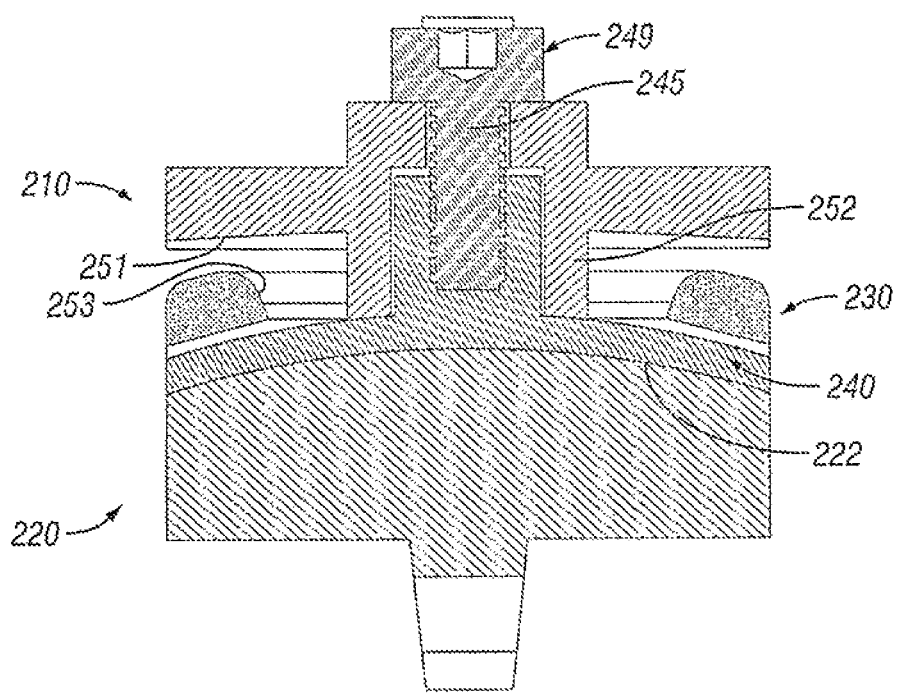
FIG. 18 is a cross sectional view of the embodiment of FIG. 16.

Second intermediate portion 240 may be generally circular in shape and may have an upper surface 241 and lower surface 242. Lower surface 242 of second intermediate member 240 is a partially spherical convex surface and may be configured to engage upper surface 222 of lower endplate 220. Lower surface 242 of second intermediate member 240 and upper surface 222 of lower endplate 200 may articulate with respect to each other in a ball and joint fashion to allow movement of adjacent vertebra relative to each other. Second intermediate portion 240 may also have protruding members 243, 244 extending from the proximal and distal ends of second intermediate portion 240, which are designed to interact with first intermediate member 230 as described in more detail below. As seen in FIG. 17, second intermediate member 240 may have a linking member 245 positioned centrally on the upper surface 241 of second intermediate member 240. In this particular design, post 245 is configured with a unique interlocking design at the superior end of post 245. Respectively, upper endplate 210 may be configured with a receiving area 247 designed to cooperate with the interlocking design of post 245. Accordingly, when assembled, second intermediate portion 240 is capable of being fixedly attached to upper endplate 210. In the embodiment illustrated in FIG. 17, the unique interlocking design of post 245 and the receiving area 247 of upper endplate 210 not only provide for a fixed connection, but also prevent the second intermediate member 240 from rotating with respect to upper endplate 210. Accordingly, to the extent the upper endplate 210 is capable of moving when attached to a vertebral body (not shown), second intermediate member 240 will move with upper endplate 210. Also as seen in FIG. 17, a fastener 249 may be provided to secure the connection between upper endplate 210 and second intermediate member 240. In this case, the fastener is an exteriorly threaded fastener that can partially pass through the receiving area 247 of upper endplate 210 and engage an internally threaded blind hole within post 245 of second intermediate portion 240. As seen in FIG. 18, lower surface 251 of upper endplate 210 may be configured with a collar 252 that is configured to receive post 245 of second intermediate portion 240. Collar 252 adds stability to the connection between the second intermediate portion 240 and the upper endplate 210.

Returning to FIG. 16, first intermediate portion 230 is fixedly attached to bottom endplate 220. As can be seen in FIG. 16, arm 231 is attached to the upper surface 222 of bottom endplate 220. First intermediate portion 230 may be generally curved to correspond to the curvature of articulating surfaces of the prosthetic disc, i.e. upper surface 222 of lower endplate 220 and lower surface 242 of second intermediate portion 240. First intermediate portion 230 may also be formed such that a cavity 236 is created between parts of the arms and generally circular portion 237 as seen in FIG. 16. As one of ordinary skill in the art would understand, a similar cavity 238 may be formed on the opposing side. Accordingly, cavities 236, 238 provide space within which portions of the second intermediate portion 240 may fit.

Referring to FIG. 18, a cross section view of the prosthetic disc of FIG. 16 is shown. In this view, fastener 249 is inserted and connects upper endplate 210 and second intermediate member 240. First intermediate member 230 is connected (connection not shown in cross section) to lower endplate 210. When assembled, second intermediate member 240 is captured by the first intermediate member 230. Even though second intermediate member 240 is captured, first intermediate member 230 is formed such that first intermediate member 230 may still articulate relative to the partially spherical convex surface 222 of lower endplate 220. As can be seen by FIG. 18, however, the degree of articulation between the respective endplates may be limited by at least the interaction of post 245 and sidewall 253 of bore hole 236 of first intermediate member 230. Accordingly, as one of ordinary skill in the art would understand, bore hole 236 and post 245 may be configured in various sizes and dimensions to control the amount of articulating between first intermediate portion 230 and lower endplate 220. First intermediate member 230 also prevents the separation of the upper endplate 210 and lower endplate 220 as the first intermediate member 230 captures the second intermediate member 240, which is fixedly attached to upper endplate 210.

Returning to FIG. 16, protruding members 256, 258 are shown extending from second intermediate member 240. Protruding members 256, 258 may extend from second intermediate member 240 at an angle, in the superior direction. As seen in FIG. 16, protruding member 256 is configured such that upon axial rotation of the prosthetic disc, protruding member 256 may contact sidewalls 257, 258 of arms 232, 233 of first intermediate member 230. Accordingly, protruding members 256, 258 may acts as stops or limits on the degree of axial rotation of the prosthetic disc. As one of ordinary skill in the art would understand, protruding members 256, 258 and arms 231-234 may be sized and dimensioned to vary the degree of axial rotation permitted by the prosthetic disc.

Figure 19:
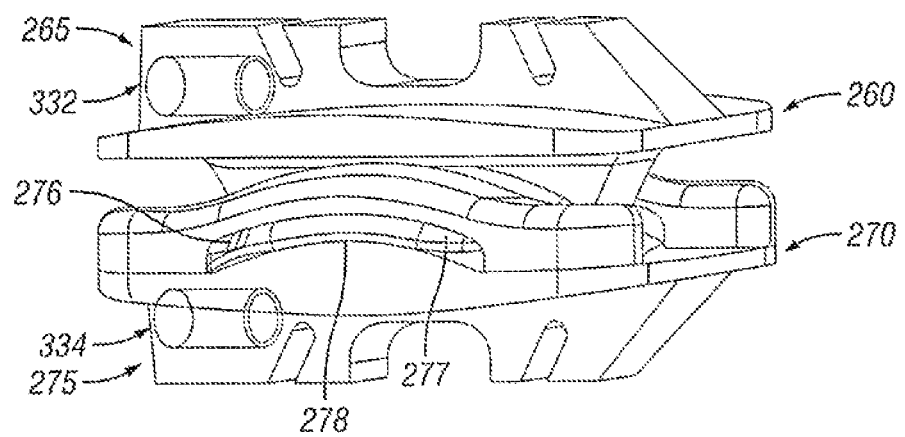
FIG. 19 is a perspective view of an embodiment of the present invention.
Figure 20:
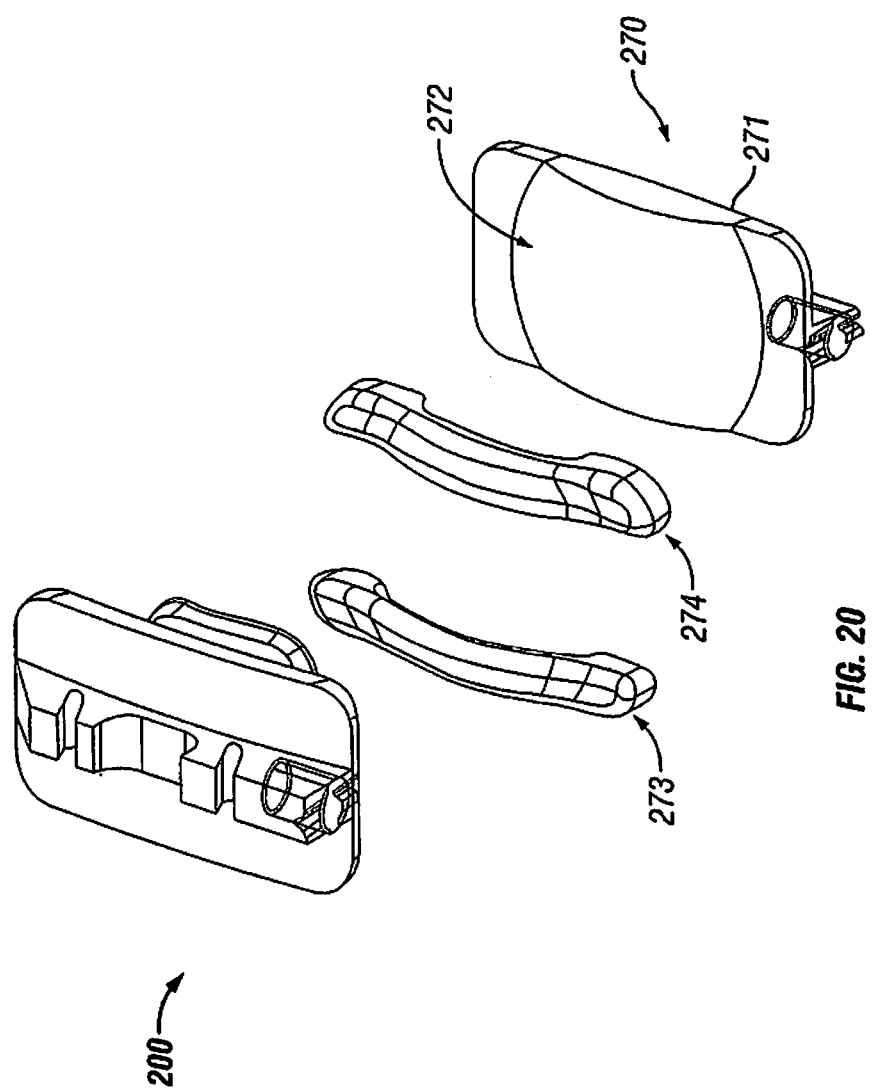
FIG. 20 is an exploded view of the embodiment of FIG. 20.

Referring to FIG. 19, an alternate embodiment of a prosthetic disc of the present invention is shown having a top endplate 260 and bottom endplate 270. Top endplate 260 may have a keel 265 with features similar to those described above. Bottom endplate 270 may also have a keel 275 with features similar to those described above. With reference to FIG. 20, an exploded view of the present prosthetic disc embodiment is provided. As seen in FIG. 20, the prosthetic disc has a top endplate 260 and bottom endplate 270. Bottom endplate 270 has a lower surface 271 and upper surface 272. Upper surface 272 of bottom endplate 270 is a partially spherical convex surface. Attached to the upper surface 272 of bottom endplate 270 are two side rails 273, 274 that run the length of lower endplate 270 and are disposed at either side of the prosthetic disc as shown in FIGS. 19 and 20. Side rails 273, 274 are each attached at two different points on the upper surface 272 of lower endplate 270. Side rails 273, 274 may be curved to match the curvature of partially spherical convex surface 272. As seen in FIG. 19, between attachment points at the ends of rail 273, a window 276 is created. Window 276 has an upper border 277 that is defined by curved rail 273 and a lower border 278 that is defined by the partially spherical convex surface 272 of lower endplate 270. One of ordinary skill in the art would understand that a similar window would be formed on the other side of the prosthetic disc.

Figure 21:
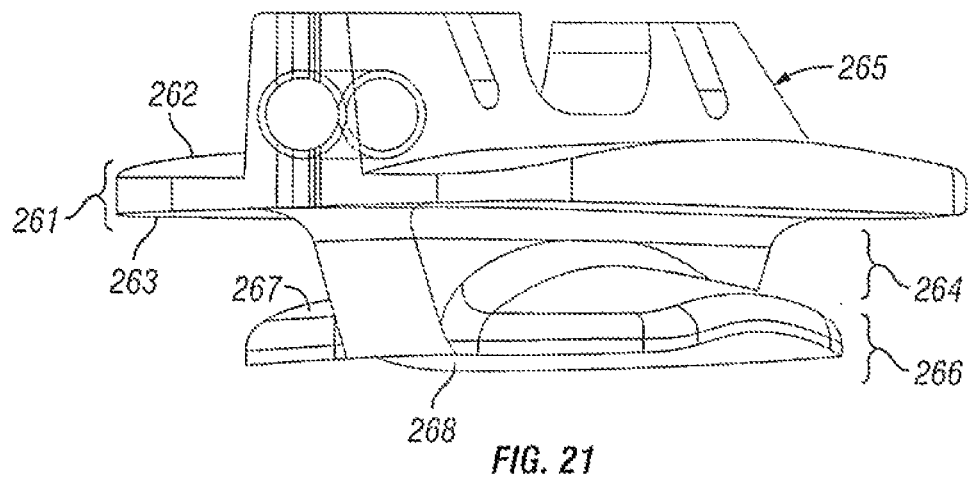
FIG. 21 is perspective view of an endplate of the embodiment of FIG. 20.

Referring to FIG. 21, top endplate 260 is shown. Top endplate 260 has three portions connected to each other. Top portion 261 has an upper surface 262 and lower surface 263, with keel 265 attached to the upper surface 262. Extending from the lower surface 263 of top portion 261 of upper endplate 260 is a middle portion 264 that extends generally along an axis of the top portion 261 and extends in the inferior direction. Middle portion 264 is configured to support bottom portion 266 of top endplate 260. As seen in FIG. 21, bottom portion 266 is connected to middle portion 264, with the middle portion creating a link between top portion 261 and bottom portion 266. Bottom portion 266 has an upper surface 267 and lower surface 268. Lower surface 268 of bottom portion 266 of upper endplate 260 is a partially spherical concave surface. Partially spherical concave surface 268 generally corresponds to partially spherical convex surface 272 of lower endplate 270. As one of ordinary skill in the art would understand, upon assembly of the prosthetic disc of the present invention, partially spherical concave surface 268 and partially spherical convex surface 272 may articulate with respect to each other, allowing the upper endplate 260 and lower endplate 270 to articulate as well. When inserted into the intervertebral space, the present design allows the vertebral bodies to move or rotate in all planes with respect to each other.

Figure 22:
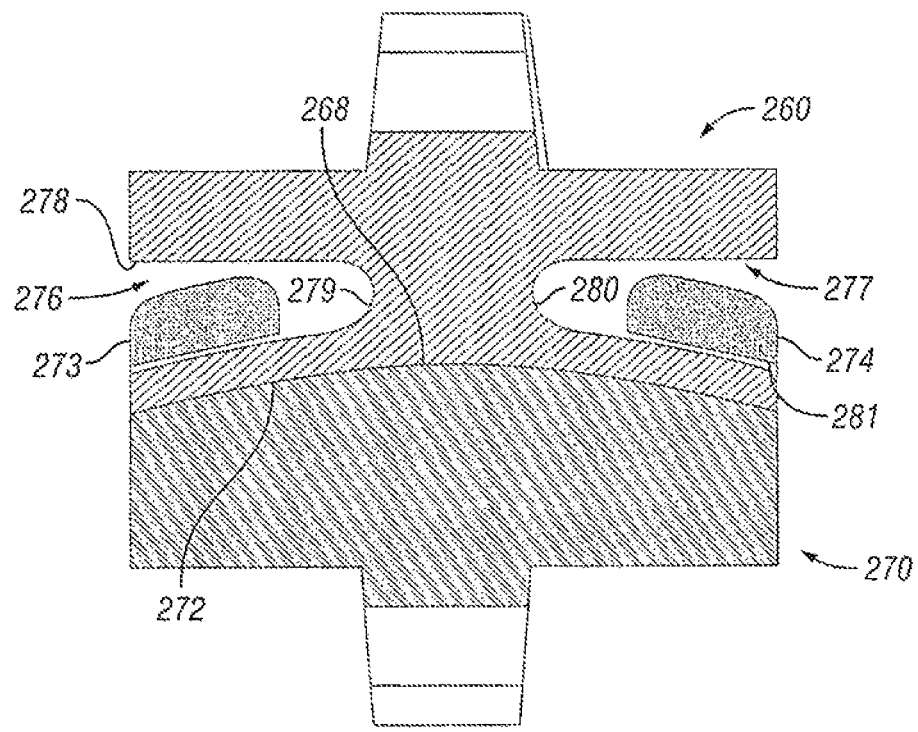
FIG. 22 is a cross sectional view of the embodiment of FIG. 20.

With reference to FIG. 22, a cross section of the embodiment of FIG. 19 is shown. In FIG. 22, the interaction between partially spherical concave surface 268 and partially spherical convex surface 272 is seen. Furthermore, FIG. 22 shows rails 273, 274 disposed between areas 276, 277, which are defined by the bottom surface 278 of top portion 261, side surfaces 279, 280 of middle portion 264, and upper surface 281 of bottom portion 266 of the top endplate 260. As one of ordinary skill in the art would understand, rails 273, 274 serve to prevent the top endplate 260 and bottom endplate 270 from separating. This feature provides a constrained design that adds stability and rigidity to the overall prosthetic disc. Not only is the device constrained from tension, i.e. separation along the longitudinal axis of the spine, but the constrained design prevents sheer translation separation, i.e. separation of the components of the prosthetic disc as a result of linear translation. Furthermore, the interaction between bottom portion 266 and rails 273, 274 as well as the interaction between rails 273, 274 and middle portion 264 serve to limit the range of rotation allowed by the articulating surfaces 268, 272. Accordingly, the prosthetic disc may be designed to provide a range of rotation. As one or ordinary skill in the art would understand, any number of changes may be made to the size, dimension, or shape of the rails, bottom portion, and/or middle portion to control the range of motion permitted by the prosthetic disc. In one embodiment, the prosthetic disc is capable of axial rotation of between about 1° and 3° In alternative embodiments, the prosthetic disc is capable of axial rotation of between about 1 degree. and 5 degree. Alternatively, the prosthetic disc is capable of axial rotation of between 1 degree and 15 degree.

Figure 23:
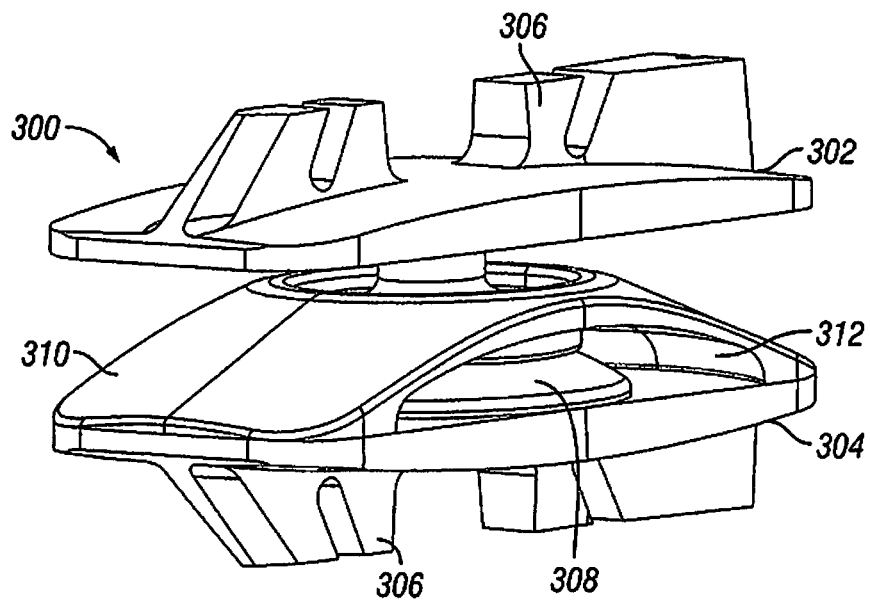
FIG. 23 is an exploded view of one particular embodiment according to the present invention.
Figure 24:
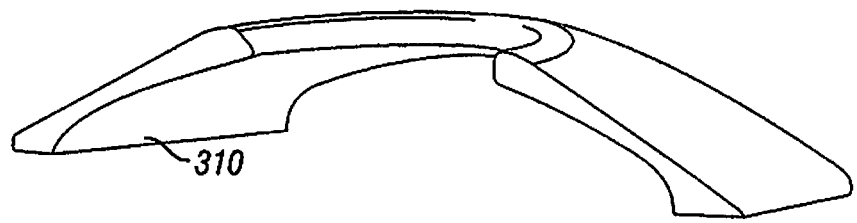

Now turning to FIG. 23, another embodiment of the present invention is illustrated. In this particular embodiment, an artificial disc 300 according to on exemplary embodiment of the present invention is shown. In this particular embodiment, the disc 300 is provided with an upper endplate 302 and a lower endplate 304. The upper endplate 302 and the lower endplate 304 are configured with keels 306 and generally composed of a titanium material. The upper endplate 302 is also provided with an extension portion 308 that extends toward the lower endplate 304. The extension portion 308 is provided with a concave lower portion that corresponds to a convex upper surface of the lower endplate 304. The extension portion 308 is enclosed by a securing element 310. The securing element 310 extends the width of the lower endplate and the length of the lower endplate enclosing the extension portion 308. The securing element 310 is provided with an access hole through which a portion of the extension portion 308 extends through to contact the upper surface of the lower endplate. On either side of the securing element 310, an opening 312 is provided from which the extension portion 308 extends through when the upper endplate 302 moves relative to the lower endplate 304. The securing element 310 constrains the motion of the upper endplate to the diameter of the access hole. The diameter of the access hole may be varied based on how much motion to constrain between the upper endplate and the lower endplate.

One consideration applicable to some embodiments of the present invention, include the desire to maintain the same degree of rotations irrespective of disc position. This may be the case when the prosthetic disc is placed into the intervertebral space through a transforaminal approach. As the prosthetic disc is seated within the vertebral space at an angle offset from either the anterior-posterior axis of the vertebral bodies and/or the medial-lateral axis of the vertebral bodies, it may be desirable to provided uniform degrees of freedom between the articulating surfaces of the prosthetic disc to accommodate natural movement in the anterior-posterior direction and medial-lateral direction as well as provided for uniform degrees of freedom for coupled motion. This freedom of movement must be designed in conjunction with the shape of the prosthetic disc such that the shape of the disc, its stops, and other structural features do not limit the degrees of freedom in one particular direction more than in others.

Another consideration in some of the embodiments of the present invention contemplate the design of prosthetic discs in shapes that complement the implantation approach. For example, prosthetic discs of a rectangular shape are particularly well configured for insertion at an oblique angle. Because the transforaminal window is small, rectangular shaped prosthetic discs provide a slim profile allowing easier insertion of the disc into the intervertebral space. Furthermore, these unique shapes also provide sufficient disc surface area to form stable contacts with the bone of the intervertebral space. Additionally, certain sizes provide improved stability of the disc itself by providing sufficient area for the articulating surface such that their respective movement is stable. All of these factors lead to disc designs with shape characteristics that make them particularly well suited for a transforaminal implantation, i.e. implantation at an oblique angle to the anterior-posterior or medial-lateral approaches. It has been found that prosthetic discs with a Length to Width ratio of about 2 to 1 are particularly well suited for transforaminal implantation in that said discs fit within the transforaminal window and provide optimum contact areas for bone contact and articulating surface area contacts. Thus for example, in one embodiment, the prosthetic disc has a length of 30 mm and a width of 15 mm. In alternative embodiments, the prosthetic disc has lengths between about 26 and 34 mm and widths of between about 13 and 16 mm.

With respect to each embodiment herein described, it would be apparent to one of ordinary skill in the art that the particular directions and configurations of the various surfaces can be modified and interchanged. Accordingly, the upper endplate may be the lower endplate and vice versa. Similarly, stops may be formed on either or both endplates. Additionally, keels may be on both or none of the endplates. Moreover, the prosthetic discs of the current invention may additionally contain any number of other features including for example, titanium sprays or other coatings or surface deposits that promote or help bony ingrowth/ongrowth. Similarly, the endplates themselves may be formed, in whole or in part, of materials or contain materials that promote bony ingrowth/ongrowth. Also, the various embodiments disclosed herein are not limited to construction out of any particular materials although metal on metal designs are one variety contemplated.

While it is apparent that the invention disclosed herein is well calculated to fulfill the objects stated above, it will be appreciated that numerous modifications and embodiments may be devised by those skilled in the art. Therefore, it is intended that the appended claims cover all such modifications and embodiments that fall within the true spirit and scope of the present invention.

What is claimed is:

1. An intervertebral prosthetic implant comprising:
a first endplate having a first surface configured to substantially engage with a first vertebral body and a second surface having a concave contact surface, the first endplate including a first keel having a slot formed therein; and
a second endplate having a second surface configured to substantially engage with a second vertebral body and a convex contact surface, the second endplate including a second keel having a slot formed therein, wherein the second endplate includes an element having a first window and an opposing second window, wherein the first window and the opposing second window open outwardly toward an outer surface of the second endplate.

2. The implant of claim 1, wherein the element having the first window and the second window is removable.

3. The implant of claim 1, wherein the element having the first window and the second window is configured with an access hole.

4. The implant of claim 3, wherein the access hole is configured to receive an extension portion that extends from the first endplate.

5. The implant of claim 4, wherein an inside radius of the element is larger than an outside radius of the extension.

6. The implant of claim 1, wherein the element having a first window and the second window is composed of a resilient material.

7. The implant of claim 1, wherein the element having a first window and the second window is composed of a PEEK material.

8. The implant of claim 1, wherein said implant is configured for implantation into an intervertebral space by a transforaminal approach.

9. An intervertebral prosthetic implant comprising:
- a first endplate having a first surface configured to substantially engage with a first vertebral body and a second surface having an extension, the first endplate including a first keel;
- a second endplate having a first surface configured to substantially engage with a second vertebral body and a second surface having an element including a first window and a second window extending therefrom, the second endplate including a second keel,
- wherein the extension of the first endplate is configured to extend through the element including the first window and the second window
- wherein the first window and the second window open outwardly toward an outer surface of the second endplate.

10. The implant of claim 9, wherein the element having the first window and the second window is removable.

11. The implant of claim 9, wherein the element having the first window and the second window is configured with an access hole.

12. The implant of claim 11, wherein the access hole is configured to receive the extension portion therethrough.

13. The implant of claim 9, wherein the first keel includes one or more slots.

14. The implant of claim 9, wherein the second keel includes one or more slots.

15. An intervertebral prosthetic implant comprising:
- a first endplate having a first surface configured to substantially engage with a first vertebral body and a second surface having an extension;
- a second endplate having a first surface configured to substantially engage with a second vertebral body and a second surface, the second endplate having a securing element configured with an access hole, and wherein the securing element includes a first window opposed from a second window;
- wherein the extension of the first endplate is configured to be received within the access hole of the second endplate,
- wherein the first window and the second window open outwardly toward an outer surface of the second endplate.

16. The implant of claim 15, wherein the first endplate has a first keel.

17. The implant of claim 15, wherein the second endplate has a second keel.

18. The implant of claim 15, wherein the securing element extends along a width and length of the lower endplate.

19. The implant of claim 15, wherein the securing element is fit coupled to the lower endplate through a welding process.

20. The implant of claim 15, wherein the securing element is composed of a PEEK material.

* * * * *